United States Patent [19]
Motoyuki et al.

[11] Patent Number: 6,018,087
[45] Date of Patent: Jan. 25, 2000

[54] ISOMERIZATION OF DIMETHYLNAPHTHALENE TO PRODUCE 2,6-DIMETHYLNAPHTHALENE

[75] Inventors: Masahiro Motoyuki, Osaka; Koji Yamamoto, Kobe; Shingo Yoshida, Osaka; Seiichi Yamamoto, Kobe, all of Japan; Ajit Vishwanath Sapre, Moorestown; John Paul Mc Williams, Woodbury, both of N.J.; Susan Patricia Donnelly, Kingwood, Tex.; Stuart Damon Hellring, Pittsburgh, Pa.

[73] Assignees: Kabushiki Kaisha Kobe Seiko Sho., Kobe, Japan; Mobil Oil Corporation, Fairfax, Va.

[21] Appl. No.: 08/948,666

[22] Filed: Oct. 10, 1997

[51] Int. Cl.$^7$ ............... C07C 5/22; C08G 63/06
[52] U.S. Cl. ............ 585/481; 585/480; 585/478; 528/361
[58] Field of Search .................. 585/480, 481, 585/478; 528/361

[56] References Cited

U.S. PATENT DOCUMENTS

| | | | |
|---|---|---|---|
| 4,777,312 | 10/1988 | Bakas et al. | 585/481 |
| 5,292,934 | 3/1994 | Sikkenga et al. | 562/413 |
| 5,723,711 | 3/1998 | Motoyuki et al. | 585/481 |
| 5,744,670 | 4/1998 | Motoyuki et al. | 585/320 |

FOREIGN PATENT DOCUMENTS 60-38331  2/1985  Japan .

OTHER PUBLICATIONS

U.S. application No. 08/887,052, filed Jul. 2, 1997.
U.S. application No. 08/948,581, filed Oct. 10, 1997.
U.S. application No. 08/948,299, filed Oct. 10, 1997.
U.S. application No. 08/948,666, filed Oct. 10, 1997.
U.S. application No. 08/974,231, filed Nov. 19, 1997, now U.S. Pat. 05,844,064.

*Primary Examiner*—Walter D. Griffin
*Assistant Examiner*—Thuan D. Dang
*Attorney, Agent, or Firm*—Oblon, Spivak, McClelland, Maier & Neustadt, P.C.

[57] ABSTRACT

The present invention relates to a method of preparing 2,6-dimethylnaphthalene from a feed stream that contains hydrocarbons which contain dimethylnaphthalene isomers. The method includes the following steps:

I. distillation and concentration of the dimethylnaphthalene isomers from the feed stream, to form a dimethylnaphthalene fraction, II. isomerization of the dimethylnaphthalene fraction to enrich the dimethylnaphthalene fraction in 2,6-dimethylnaphthalene, to form a 2,6-enriched dimethylnaphthalene fraction, III. purification of 2,6-dimethylnaphthalene from the 2,6-enriched dimethylnaphthalene fraction, wherein step II is conducted in the presence of a catalyst composition containing a synthetic zeolite characterized by an X-ray diffraction pattern including interplanar d-spacing (Å)

12.36±10.4
11.03±0.2
8.83±10.14
6.18±0.12
6.00±0.10
4.06±0.07
3.91±0.01
3.42±0.06, wherein the purification includes crystallization under pressure.

8 Claims, 5 Drawing Sheets

FIG. 2 (HIGH-PRESSURE CRYSTALLIZATION -1)

FIG. 3 (HIGH- PRESSURE CRYSTALLIZATION -2)

FIG. 4 (HIGH-PRESSURE CRYSTALLIZATION -3)

ISOMERIZATION OF DIMETHYLNAPHTHALENE TO PRODUCE 2,6-DIMETHYLNAPHTHALENE

BACKGROUND OF THE INVENTION

FIELD OF THE INVENTION

The present invention relates to a process for producing and obtaining 2,6-dimethylnaphthalene (2,6-DMN) from a mixtures of which contains dimethylnaphthalenes.

DISCUSSION OF THE BACKGROUND

The compound 2,6-DMN is useful as a precursor of 2,6-naphthalenedicarboxylic acid, used in the manufacture of high performance polyester resins such as polyethylene naphthalate polymer (PEN) or polybutyrene naphthalate polymer (PBN), because 2,6-DMN is easily oxidized to 2,6-naphthalenedicarboxylic acid compared with other precursors such as 2,6-diisopropylnaphthalene or 2-methyl-6-isobutytylnaphthalenes. There have been many expected PEN's applications to film and bottle uses, long time recording type video film, Advanced Photo System, hot fill containers, refillable bottles and tire codes because of its good physical properties in strength, thermal resistance and gas barrier properties. PBN's main applications are expected to be for electronics, insulators and car parts.

However, PEN and PBN are presently too expensive to expand into these markets cleanly because of there are few effective processes for the commercial preparation of 2,6-DMN.

There have been many proposals concerning the process for preparing 2,6-DMN.

U.S. Pat. No. , 4,795,847 (Weitkamp et al.) describes a process for the preparation of 2,6-dialkylnaphthalene by alkylating naphthalene or 2-alkyl-naphthalene with an alkylating agent in the presence of a zeolite (specifically ZSM-5) as a catalyst.

U.S. Pat. No. 5,001,295 (Angevine et al.) describes a process for preparing DMN by using 2-monomethylnaphthalene (MMN) and naphthalene as a feedstock and a synthetic zeolite (MCM-22) as a catalyst, and it shows that MCM-22 is more effective than ZSM-5 in alkylation of 2-MMN and naphthalene.

However these methods provide only for batchwise operation for alkylation of 2-MMN, which is an expensive feedstock and is not available in large amounts commercially.

U.S. Pat. Nos. 4,990,717 (Sikkenga) and 5,073,670 (Sikkenga et al.) describe a multi-step process to produce 2,6-DMN from o-xylene and butadiene, which consists of:

1) preparation of 5-(o-tolyl)-pentene-2 (OTP) by alkenylation of o-xylene with butadiene in the presence of a catalyst such as an alkali metal catalyst;
2) preparation of 1,5-dimethyltetralin (1,5-DMT) by cyclization of OTP in the presence of a catalyst such as platinum and copper on an ultra stable zeolite catalyst;
3) preparation of 1,5-dimethylnaphthalene (1,5-DMN) by dehydrogenation of 1,5-DMT in the presence of a catalyst such as platinum and rhenium on gamma-alumina; and
4) preparation of a DMN mixture which is rich in the desirable 2,6-DMN, 1,6-DMN and 1,5-DMN by isomerization of 1,5-DMN in the presence of a catalyst such as a beta-zeolite catalyst.

If a 2,6-DMN separation from DMN mixture were combined with the above multi-step process, a complete process to produce purified 2,6-DMN could be provided.

As a multi-step process makes the process plant complicated and operate at a high cost, it is hard to say that this method is a definitive process for an economical preparation of purified 2,6-DMN on a commercial scale.

Furthermore, it is very difficult to separate 2,6-DMN from other isomers by conventional separation methods such as by distillation and by cooling crystallization because;

1) There is very small difference in boiling points of each DMN isomers, specifically the difference in boiling points between 2,6-DMN and 2,7-DMN is only 0.3° C., where it is nearly impossible to efficiently separate 2,6-DMN by distillation.
2) The cooling of a DMN isomer mixture solution for 2,6-DMN purification forms a precipitate of very fine 2,6-DMN crystals in suspension, where separation of the 2,6-DMN is extremely difficult.

Koide et al U.S. Pat. No. 4,992,619 reports a method of separating a methyl derivative of naphthalene from a mixture material in a high purity, by crystallization under a pressure.

Moritoki et al U.S. Pat. No. 4,784,766 reports a pressure crystallization apparatus.

Accordingly, methods of economically preparing 2,6-dimethylnaphthalene are sought.

SUMMARY OF THE INVENTION

According to one embodiment of the invention is a method of preparing 2,6-dimethylnaphthalene.

According to another embodiment of the present invention is a method of preparing a polyester resin.

These and other objects of the present invention are made possible by a method in which dimethylnaphthalenes are extracted from a hydrocarbon stream, enriched in 2,6-dimethylnaphthalene by isomerization, then 2,6-dimethylnaphthalene is purified, wherein isomerization is conducted with a synthetic zeolite characterized by an X-ray diffraction pattern including interplanar d-spacing 12.36±10.4
11.03±0.2
8.83±0.14
6.18±0.12
6.00±0.10
4.06±0.07
3.91±0.07
3.42±0.06 Å.

The present invention provides an effective production process of 2,6-DMN as a high-value added product by utilizing a non valuable feed stream.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
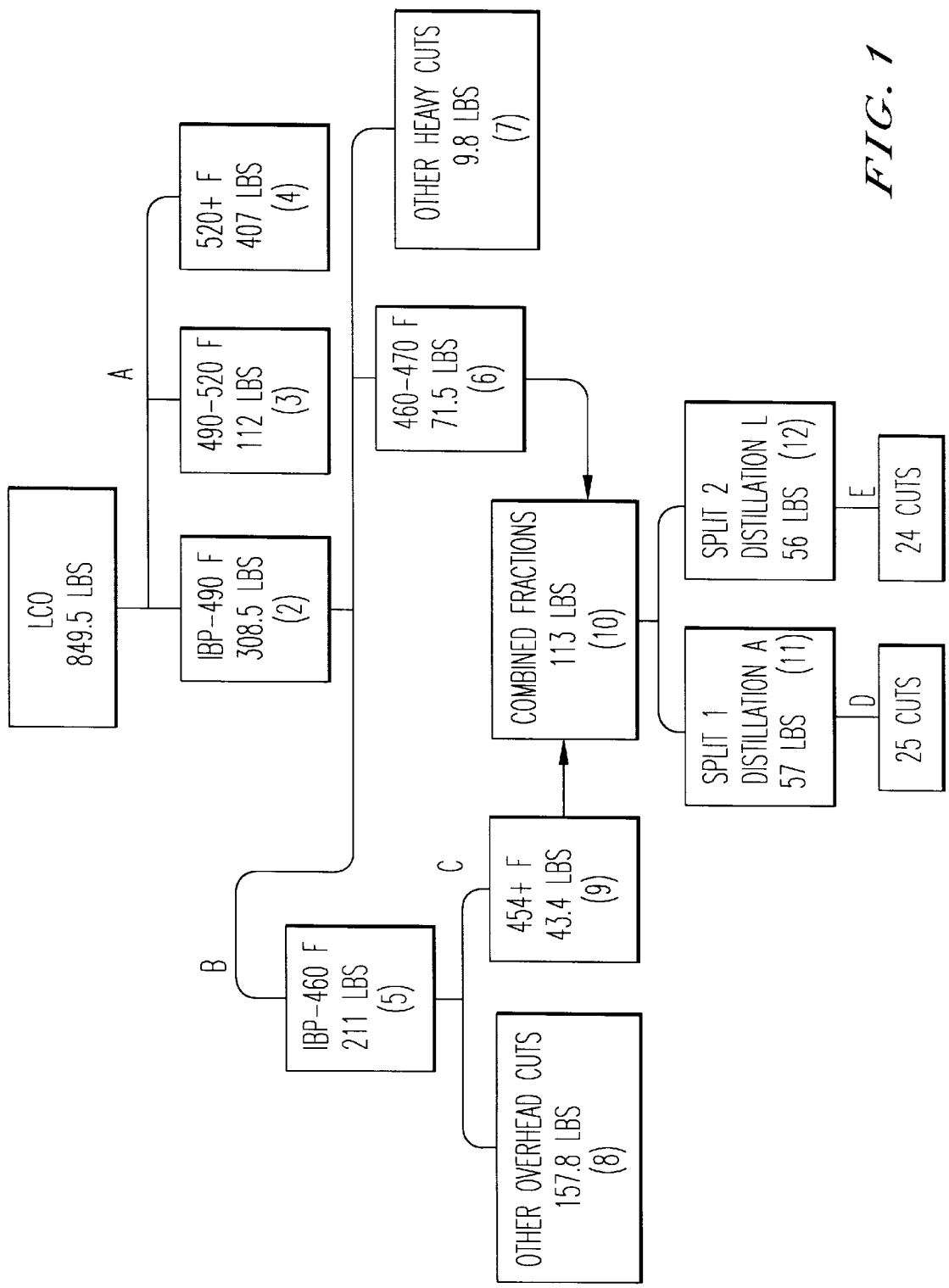
FIG. 1, illustrates product separation of several fractions by the difference in boiling point.

The present invention can be applied to any feed stream of hydrocarbons that contains DMN isomers including 2,6-DMN and/or 1,6-DMN. A non-limiting example includes, LCO (Light Cycle Oil) from FCC (Fluid Catalytic Cracking) or HC (Hydrocracker) as a preferable as feed stream. Refinery plants usually have FCC or HC for gasoline recovery from residues of atmospheric distillation units. LCO is a by-product and its main use is for a diluent of A-heavy oil and/or C-heavy oil by being mixed with them. Therefore, LCO has heretofore been known to have fuel value.

However, LCO usually contains a DMN fraction at about 10–30 weight %. (DMNs/LCO), wherein the 2,6-DMN content and 1,6-DMN content in the DMN fraction is about 10–20%, and 10–20% respectively. (2,6-DMN/DMNS, 1,6-DMN/DMNS)

Separation of DMSN from the feed stream may be conducted by conventional separation techniques known to those of ordinary skill in the art, such as by distillation. The efficiency of distillation may by increased by conventional techniques such as counter current flow or the like.

Isomerization conditions are those generally as disclosed in co-pending application U.S. Ser. No. 08/661,114, as suitable for conducting simultaneous transalkylation of dialkylnaphthalene and naphthalene, and isomerization of dialkylnaphthalenes, the relevant portions of which are hereby incorporated by reference.

As a suitable catalyst for isomerisation, a synthetic zeolite characterized by an X-ray diffraction pattern including interplanar d-spacing and relative intensity $I/I_o \times 100$

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-VS |
| 4.06 ± 0.07 | W-S |
| 3.91 ± 0.07 | M-VS |
| 3.42 ± 0.06Å | VS. |

A suitable catalyst is described in U.S. Pat. No. 5,001,295, as MCM-22, the entire contents of which are hereby incorporated by reference.

Preferably, isomerization is conducted at a weight hourly space velocity (WHSV) of dimethylnaphthalenes of 0.1 to 10, preferably 0.5 to 5 $h^{-1}$, more preferably 0.75 to 1.5 $h^{-1}$.

Preferably, isomerization is conducted at a temperature of from 100 to 500° C., preferably 150 to 350° C., more preferably 200 to 300° C.

Preferably, isomerization is conducted at a pressure of atmospheric to 100 $kgf/cm^2$, preferably atmospheric to 30 $kgf/cm^2$.

During isomerization it is possible to co-feed of hydrogen, but is not always necessary, in an amount of 0.1 to 10 $mol-H_2/mol$-hydrocarbons.

Separation of 2,6-dimethylnaphthalene maybe conducted by using crystallization under high pressure. In general, a liquid mixture containing two or more substances is pressurized, and a certain substance in the mixture is solidified and separated from the residual liquid by the effect of the pressure. In other words, this method involves a separating and purifying technique wherein a liquid mixture containing two or more substances is placed in a tightly sealed pressure vessel, a portion of the desired substance, 2,6-dimethylnaphthalene, is solidified to form a solid-liquid co-existing state, the liquid is discharged from the co-existing system while maintaining the pressure of the solid-liquid co-existing system at a higher level than equilibrium pressure of the objective substance, then the solid remaining in the vessel is pressed for discharging the residual liquid between the solid particles and integrating the solid particles. This technique is generally described in U.S. Pat. No. 5,220,098.

The method involves injecting the slurry or liquid of the temperature of 30 to 120° C., preferably 80 to 100° C., into a high pressure vessel for conducting a crystallization under high pressure; adiabatically pressurizing the vessel to a pressure of from 300 to 4,000 $kgf/cm^2$, preferably 500 to 2,000 $kgf/cm^2$ to increase the quantity, i.e. the amount of 2,6-dimethylnaphthalene crystals, whereby coexistence of solid-liquid phases exist at the high pressure conditions; discharging the liquid phase component from the high pressure vessel, the discharging being conducted under pressure, to increase the ratio of the solid phase relative to the liquid phase within the vessel; lowering the pressure of the residual liquid phase so as to dissolve partially and purify the solid phase; discharging the residual liquid phase by applying pressure to the solid phase within the high pressure vessel whereby a 2,6-dimethylnaphthalene crystal block having a high purity is obtained within the high pressure vessel. By this technique, a purity of 2,6 dimethylnaphthalene of ≧98% by weight, preferably ≧99% by weight may be obtained.

The resulting 2,6-dimethylnaphthalene may then be used to produce a polyester resin, by oxidation of 2,6-dimethylnaphthalene to form 2,6-naphthalenedicarboxylic acid, by conventional methods known to those of ordinary skill in the art.

The 2,6-naphthalenedicarboxylic acid may then be condensed with a diol such as ethylene glycol, propylene glycol, butane diol, pentane diol and hexane diol. In a preferred embodiment, the polyester resin formed in a polyethylenenaphthalate or polybutylenenaphthalate resin. Such a condensation may be conducted by conventional methods known to those of ordinary skill in the art.

Alternatively a polyester resin may be formed from 2,6-naphthalenedicarboxylic acid by first esterification of 2,6-naphthalenedicarboxylic acid with an alcohol such as a $C_{1-6}$ alcohol, such as methanol, ethanol, propanol, isopropanol, n-butanol, s-butanol, i-butanol, t-butanol. In a preferred embodiment, the alcohol is methanol. Esterification may be conducted by conventional techniques known to those of ordinary skill in the art. The alkylester of 2,6-naphthalenedicarboxylic acid by then be condensed with a diol as described above, by conventional methods known to those of ordinary skill in the art. Suitable diols include ethylene glycol, propylene glycol, butane diol, pentane diol and hexane diol. In a preferred embodiment the diol is either ethylene glycol or butane diol.

Having generally described this invention, a further understanding can be obtained by reference to certain specific examples which are provided herein for purposes of illustration only and are not intended to be limiting unless otherwise specified.

EXAMPLE 1

(Isomerization)

20 grams of MCM-22 (1/16 "D×3/8 'L, cylindrical pellets) are charged in a tubular reactor (volume: 122 cc). The reactor was heated from room temperature to 400° C. at the rate of 100° C./hr over introducing nitrogen gas into the reactor at atmospheric pressure.

As a feed stock for isomerization, a mixture of DMN isomers was used. The feedstock was supplied to the reactor (250° C.) at the rate of 20.0 g/hr for 6 hours. The obtained product was analyzed by gas chromatography, and the result is summarized in Table 1.

TABLE 1

| | Isomerization | |
|---|---|---|
| | before reaction | after reaction |
| Light components | 8.8 | 6.26 |
| naphthalene | | 0 |
| 2-MMN | 0.15 | 1.6 |
| 1-MMN | 0.61 | 0.78 |
| 2,6-DMN | 10.97 | 15.63 |
| 2,7-DMN | 12.65 | 14.53 |
| 1,6-DMN | 18.72 | 14.8 |
| 1,3-+1,7-DMN | 32.49 | 27.75 |
| 1,4-DMN | 2.95 | 2.8 |
| 1,2-+1,5-DMN | 3.83 | 3.85 |
| 2,3-DMN | 4.22 | 7.1 |
| 1,8-DMN | 0 | 0 |
| Heavy components | 0.19 | 1.95 |
| 2-EN (Ethylnaphthalene) | 1.48 | 1.68 |
| 1-EN | 0.54 | 0 |
| | 0 | 0 |
| | 0 | 0 |
| Total Heavy | 0.19 | 1.95 |
| Total DMN | 85.83 | 86.46 |
| Total MN | 0.76 | 2.38 |
| Total | 97.6 | 98.73 |
| 2,6-DMN/2,7-DMN[−] | 0.87 | 1.08 |
| 2,6-DMN Group Selectivity [%] | 36.82 | 37.42 |
| 2,6-DMN Selectivity [%] | 12.78 | 18.08 |

| TRA-: | 351-2 |
|---|---|
| Temp[° C.]: | 250.0 |
| Press[Kg/cm$^2$]: | 5.0 |
| Feed: | LCO |
| WHSV[1/h]: | 1.0 |

*1)2,6-Group Selectivity = 2,6-DMN Group(2,6-+1,6-+1,5-)/Total DMNs
*2)2,6-DMN Selectivity = 2,6-DMN/Total DMNs As can be seen in Table 1, 2,6-DMN can be enriched effectively by the present invention.

EXAMPLE 2

(Purification)

Pre-condensation of 2,6-DMN from LCO Blend-1 and Blend-2 was tried by cooling crystallization and a 2,6-DMN rich cake, which is to be used as a feed stock for the crystallization under high pressure, was separated by bench scale pressure filtration unit.

Purification of 2,6-DMN from the 2,6-DMN rich cake was carried out by the crystallization under high pressure method using Kobelco's HPC test machine.

Figure 2:
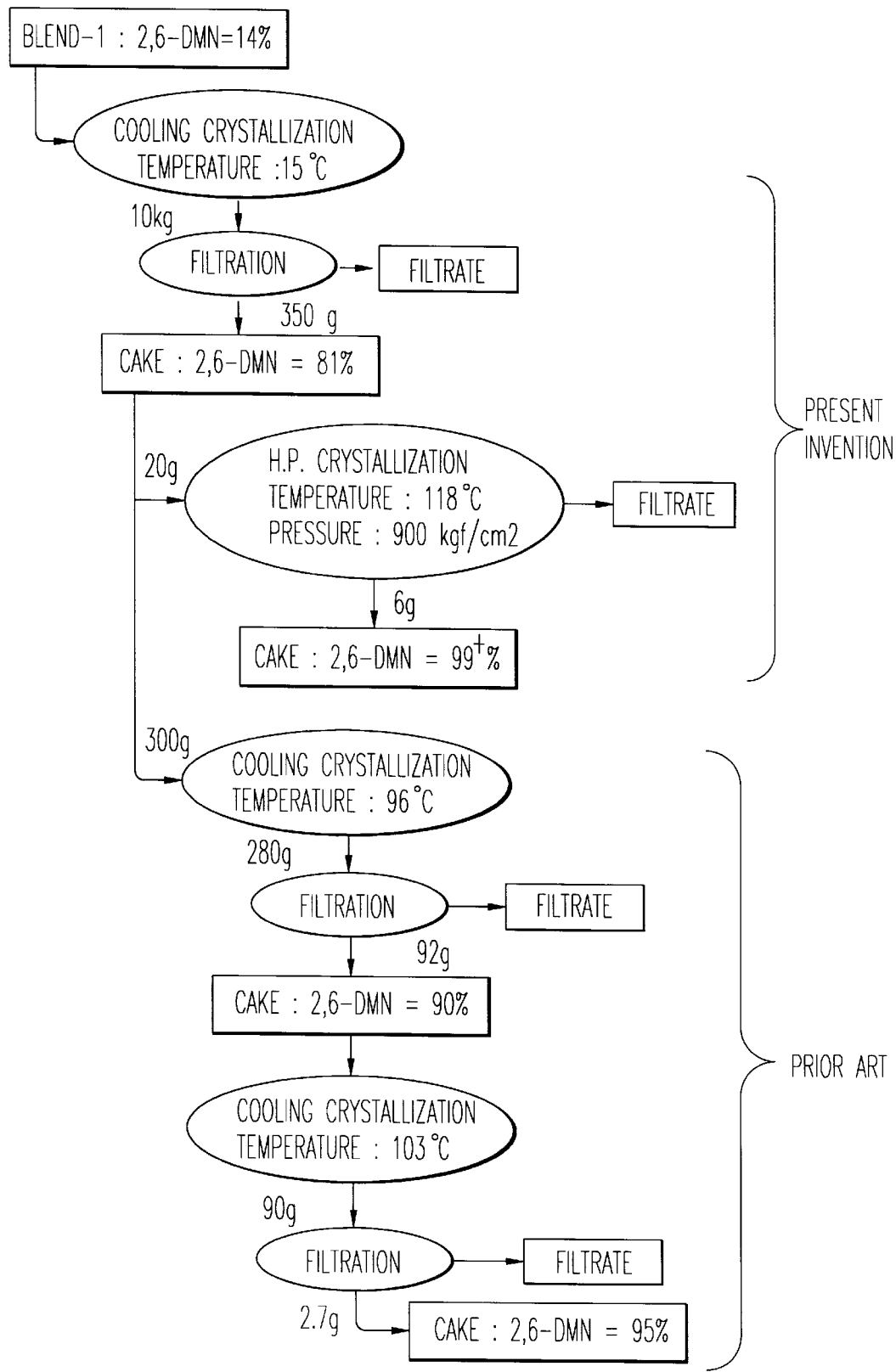
FIGS. 2–4, illustrates a crystallization scheme incorporating crystallization under high pressure.
Figure 3:
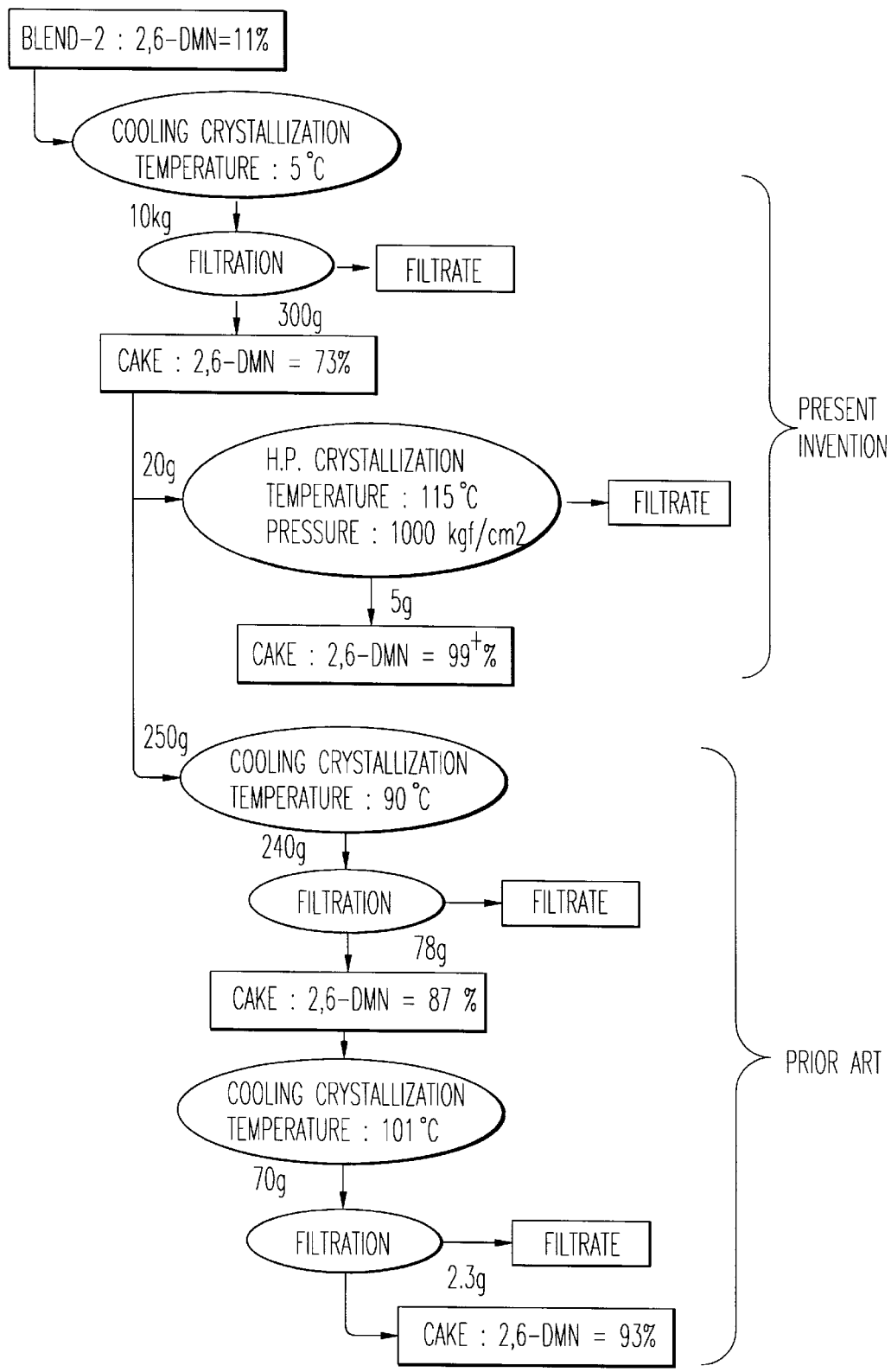

Several series of experiments were performed and results are summarized in FIG. 2 and FIG. 3.

As can be seen in FIG. 2 and FIG. 3, crystallization under high pressure achieves much effective purification performance in separation yield and 2,6-DMN purity by single stage crystallization than two-stages Cooling Crystallization.

EXAMPLE 3

(Purification)

Figure 4:
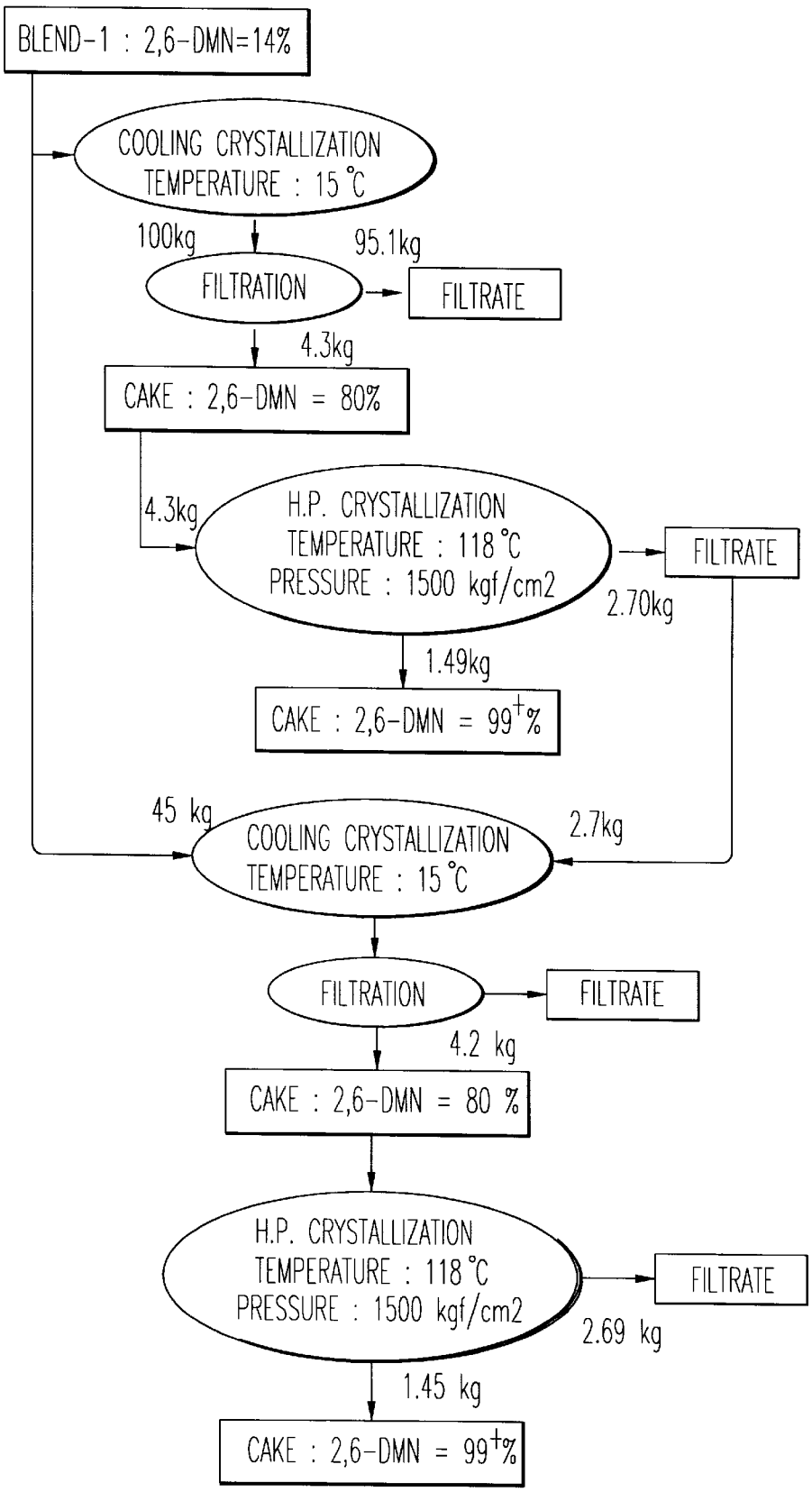
Figure 5:
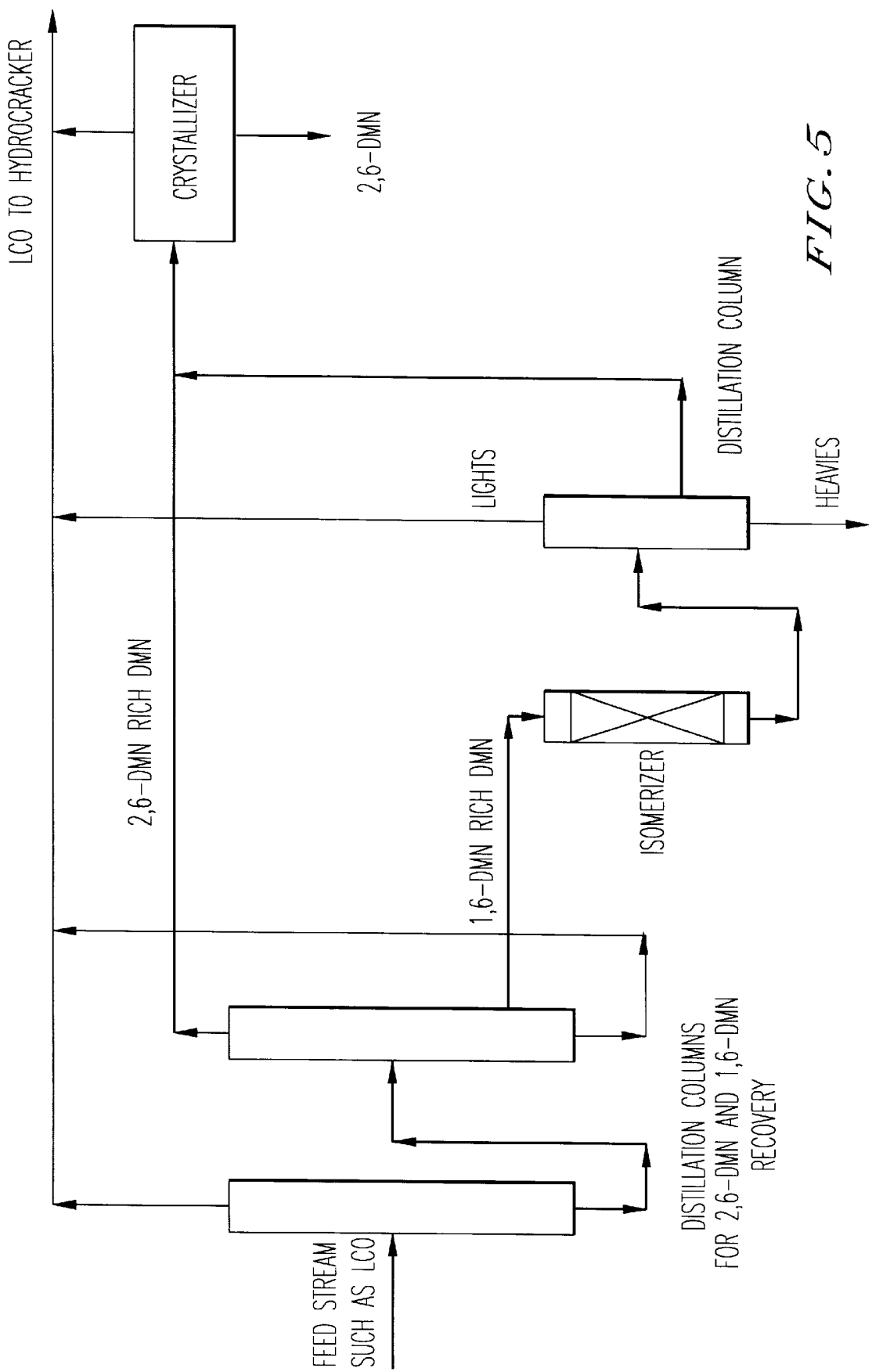
FIG. 5 illustrates a process flow according to one embodiment of the present invention.

As shown in FIG. 4, crystallization under high pressure can achieve high purity of 2,6-DMN more than 99% effectively.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing 2,6-dimethylnaphthalene from a feed stream comprising hydrocarbons which contain dimethylnaphthalene isomers comprising the following steps:
   I. distillation and concentration of said dimethylnaphthalene isomers from said feed stream, to form a dimethylnaphthalene fraction,
   II. isomerization of said dimethylnaphthalene fraction to enrich said dimethylnaphthalene fraction in 2,6-dimethylnaphthalene, to form a 2.6-enriched dimethylnaphthalene fraction,
   III. purification of 2,6-dimethylnaphthalene from said 2,6-enriched dimethylnaphthalene fraction,
wherein step II is conducted in the presence of a catalyst composition comprising a synthetic zeolite characterized by an X-ray diffraction pattern including interplanar d-spacing (Å)

12.36±0.4

11.03±0.2

8.83±0.14

6.18±0.12

6.00±0.10

4.06±0.07

3.91±0.01

3.42±0.06, wherein said purification comprises crystallization under pressure.

2. The process of claim 1, further comprising separation, from said dimethylnaphthalene isomers or said 2,6-enriched dimethylnaphthalene fraction of a 2,6-rich-dimethylnaphthalene stream and a 1,6-rich-dimethylnaphthalene stream.

3. The process of claim 2, wherein said 1,6-rich-dimethylnaphthalene stream is fed to step II to be enriched in 2,6-dimethylnaphthalene.

4. The process of claim 2, wherein one or both of the 2,6-rich-dimethylnaphthalene streams obtained from said dimethylnaphthalene isomers and said 2,6-enriched dimethylnaphthalene fraction are fed to step III.

5. A process of preparing a polyester resin comprising:
   A. oxidizing 2,6-dimethylnaphthalene to form 2,6-naphthalenedicarboxylic acid, and
   B. condensing said 2,6-naphthalenedicarboxylic acid with a diol to form a polyester resin
   wherein the said 2,6-dimethylnaphthalene is produced by the process as defined in claim 1.

6. The process of claim 5, wherein said diol is selected from the group consisting of ethylene glycol and butane diol.

7. A process of preparing a polyester resin comprising;
   A. oxidizing 2,6-dimethylnaphthalene to form 2,6-naphthalenedicarboxylic acid; and
   B. esterifying 2,6-naphthalenedicarboxylic acid with methanol to form dimethyl-2,6-naphthalenedicarboxylate; and
   C. condensing said dimethyl-2,6-naphthalenedicarboxylate with a diol to form a polyester resin,
   wherein the said 2,6-dimethylnaphthalene is produced by the process as defined in claim 1.

8. The process of claim 7, wherein said diol is selected from the group consisting of ethylene glycol and butane diol.

* * * * *